US011564557B2

(12) United States Patent
Sato et al.

(10) Patent No.: US 11,564,557 B2
(45) Date of Patent: Jan. 31, 2023

(54) MEDICAL INSTRUMENT FOR ENDOSCOPIC USE

(71) Applicant: Olympus Corporation, Hachioji (JP)

(72) Inventors: Yukio Sato, Kokubunji (JP); Yasuhiro Tabuchi, Hino (JP); Yuya Hidaka, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 562 days.

(21) Appl. No.: 16/710,709

(22) Filed: Dec. 11, 2019

(65) Prior Publication Data

US 2020/0113420 A1    Apr. 16, 2020

Related U.S. Application Data

(63) Continuation of application No. PCT/JP2017/023597, filed on Jun. 27, 2017.

(51) Int. Cl.
| | |
|---|---|
| *A61B 1/00* | (2006.01) |
| *A61B 1/018* | (2006.01) |
| *A61B 17/29* | (2006.01) |
| *A61B 17/295* | (2006.01) |

(52) U.S. Cl.
CPC ...... *A61B 1/00135* (2013.01); *A61B 1/00082* (2013.01); *A61B 1/018* (2013.01); *A61B 17/29* (2013.01); *A61B 17/295* (2013.01)

(58) Field of Classification Search
None
See application file for complete search history.

(56) References Cited

U.S. PATENT DOCUMENTS

| | | | | |
|---|---|---|---|---|
| 6,352,503 | B1* | 3/2002 | Matsui | A61B 1/00154 600/106 |
| 2005/0222495 | A1* | 10/2005 | Okada | A61B 1/018 600/114 |
| 2005/0228224 | A1* | 10/2005 | Okada | A61B 17/3421 600/153 |

(Continued)

FOREIGN PATENT DOCUMENTS

| | | |
|---|---|---|
| JP | 2005-334237 A | 12/2005 |
| JP | 2006-334398 A | 12/2006 |

(Continued)

OTHER PUBLICATIONS

Sep. 19, 2017 Written Opinion issued in International Patent Application No. PCT/JP2017/023597.

(Continued)

*Primary Examiner* — Timothy J Neal
(74) *Attorney, Agent, or Firm* — Oliff PLC

(57) ABSTRACT

The disclosed technology is directed to a medical instrument for endoscopic use. The medical instrument comprises an elongated open ended over tube configured to receive an endoscope in a direction along a longitudinal central axis of the over tube. The endoscope travels retractably from a distal end of the over tube. A tube is disposed concentrically outwardly of the over tube so that a treatment tool is inserted through the tube and is projected forwardly with respect to the over tube from a distal end of the tube. A balloon is disposed on an external surface of the over tube and is expandable outwardly in a radial direction of the over tube.

9 Claims, 9 Drawing Sheets

(56) References Cited

U.S. PATENT DOCUMENTS

| | | | |
|---|---|---|---|
| 2005/0261674 A1* | 11/2005 | Nobis | A61B 1/012 606/45 |
| 2005/0267335 A1* | 12/2005 | Okada | A61B 1/00183 600/173 |
| 2011/0245610 A1 | 10/2011 | Tanaka | |
| 2013/0184528 A1 | 7/2013 | Onuki et al. | |
| 2016/0135666 A1 | 5/2016 | Hashimoto et al. | |
| 2018/0132705 A1 | 5/2018 | Higuchi | |
| 2018/0206711 A1* | 7/2018 | Piskun | A61B 17/29 |

FOREIGN PATENT DOCUMENTS

| | | |
|---|---|---|
| JP | 2010-029487 A | 2/2010 |
| JP | 2011-083487 A | 4/2011 |
| JP | 2011-212096 A | 10/2011 |
| JP | 2013-052258 A | 3/2013 |
| WO | 2015/019753 A1 | 2/2015 |
| WO | 2016/190324 A1 | 12/2016 |

OTHER PUBLICATIONS

Sep. 19, 2017 International Search Report issued in International Patent Application No. PCT/JP2017/023597.

* cited by examiner

MEDICAL INSTRUMENT FOR ENDOSCOPIC USE

CROSS-REFERENCE TO RELATED APPLICATION

This application is a continuation application of PCT Application No. PCT/JP2017/023597 filed on Jun. 27, 2017, which is hereby incorporated by reference in its entirety.

TECHNICAL FIELD

The disclosed technology relates to a medical instrument for endoscopic use.

DESCRIPTION OF THE RELATED ART

A Japanese Patent Application JP 2005-334237 (PTL 1) discloses a coupling tool for attaching guiding tubes to direct treatment tools to a distal end of an inserting portion of an endoscope.

According to this coupling tool, it is possible to treat an affected part while disposing and observing, within a field of view of the endoscope, distal ends of the treatment tools guided via the guiding tubes disposed on an outside in a radial direction of the inserting portion of the endoscope.

However, the coupling tool of PTL 1 attaches the guiding tubes directing the treatment tools, to a distal end of the inserting portion of the endoscope. Thus, when a curved portion of the endoscope is operated to perform treatment by a treatment tool introduced via a channel of the endoscope, the treatment tools directed via the guiding tubes are also moved in synchronism with the operation of the endoscope. The treatment may therefore become difficult. For example, in a case where a treatment of cutting a tissue by the treatment tool passed through the channel of the endoscope is performed by operating the curved portion of the endoscope while a surrounding tissue is raised by the treatment tools passed via the guiding tubes, the treatment becomes difficult when the treatment tools raising the tissue are also moved so as to follow the operation of the endoscope.

BRIEF SUMMARY OF EMBODIMENTS

One aspect of the disclosed technology is directed to a medical instrument for endoscopic use. The medical instrument comprises an elongated open ended over tube configured to receive an endoscope in a direction along a longitudinal central axis of the over tube. The endoscope travels retractably from a distal end of the over tube. A tube is disposed concentrically outwardly of the over tube so that a treatment tool is inserted through the tube and is projected forwardly with respect to the over tube from a distal end of the tube. A balloon is disposed on an external surface of the over tube and is expandable outwardly in a radial direction of the over tube.

Another aspect of the disclosed technology is directed to a medical instrument for endoscopic use. The medical instrument comprises an elongated open ended over tube configured to receive an endoscope in a direction along a longitudinal central axis of the over tube. The endoscope travels retractably from a distal end of the over tube. A first tube is disposed concentrically outwardly of the over tube so that the treatment tool is inserted through the first tube and is projected forwardly with respect to the over tube from a distal end of the first tube. A second tube is disposed concentrically outwardly of the over tube so that a treatment tool is inserted through the second tube and is projected forwardly with respect to the over tube from a distal end of the second tube so as to be separated from the first tube. A balloon is disposed on an external surface of the over tube and is expandable between the first tube and the second tube and outwardly in a radial direction of the over tube and the balloon at a time of expansion being located radially outwardly of the first tube and the second tube.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

The disclosed technology has been made in view of the circumstances described hereinbefore. It is an object of the disclosed technology to provide a medical device that can facilitate treatment by allowing a treatment tool directed into a field of view of an endoscope via an outside of the endoscope to be operated independently of the movement of the endoscope.

A medical instrument for endoscopic use 1 according to one embodiment of the disclosed technology will be described in the following with reference to the drawings.

Figure 1:
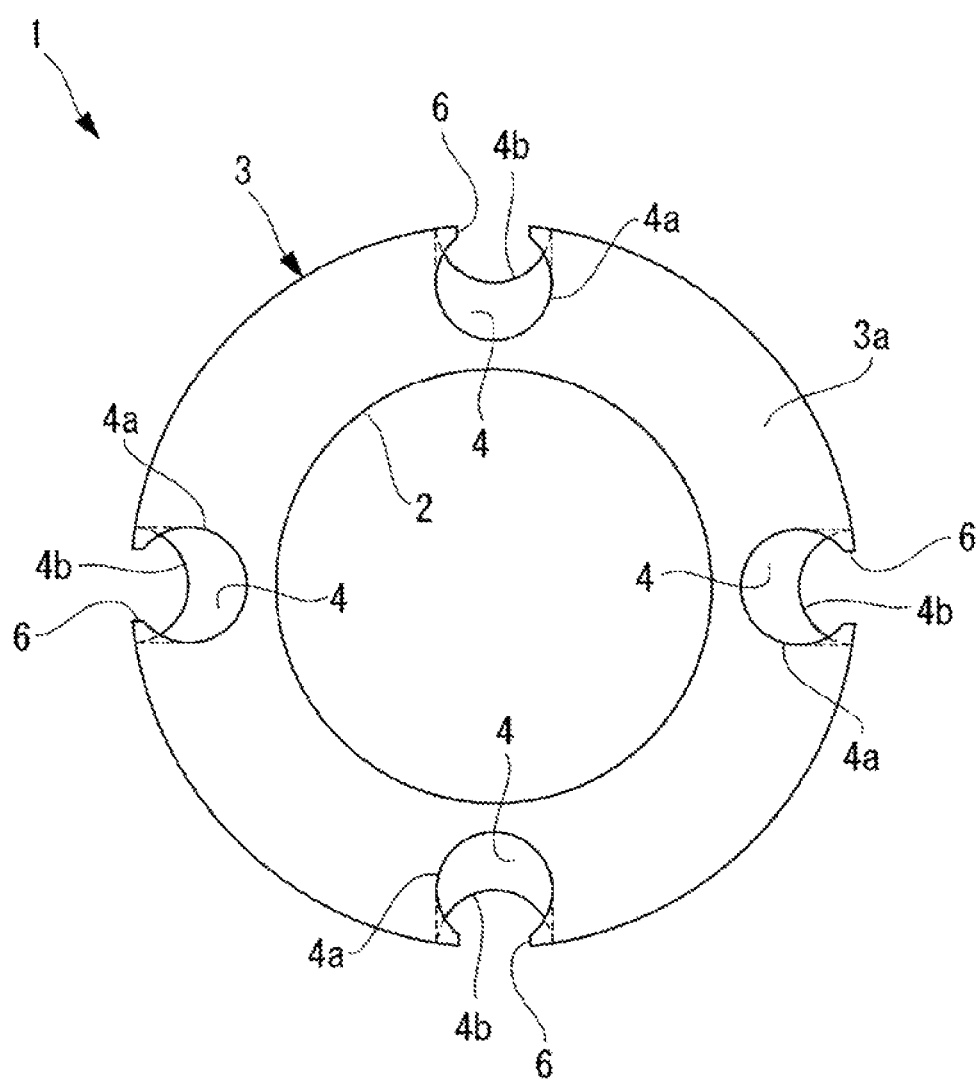
FIG. 1 is a front view depicting a medical instrument for endoscopic use according to one embodiment of the disclosed technology.
Figure 2:
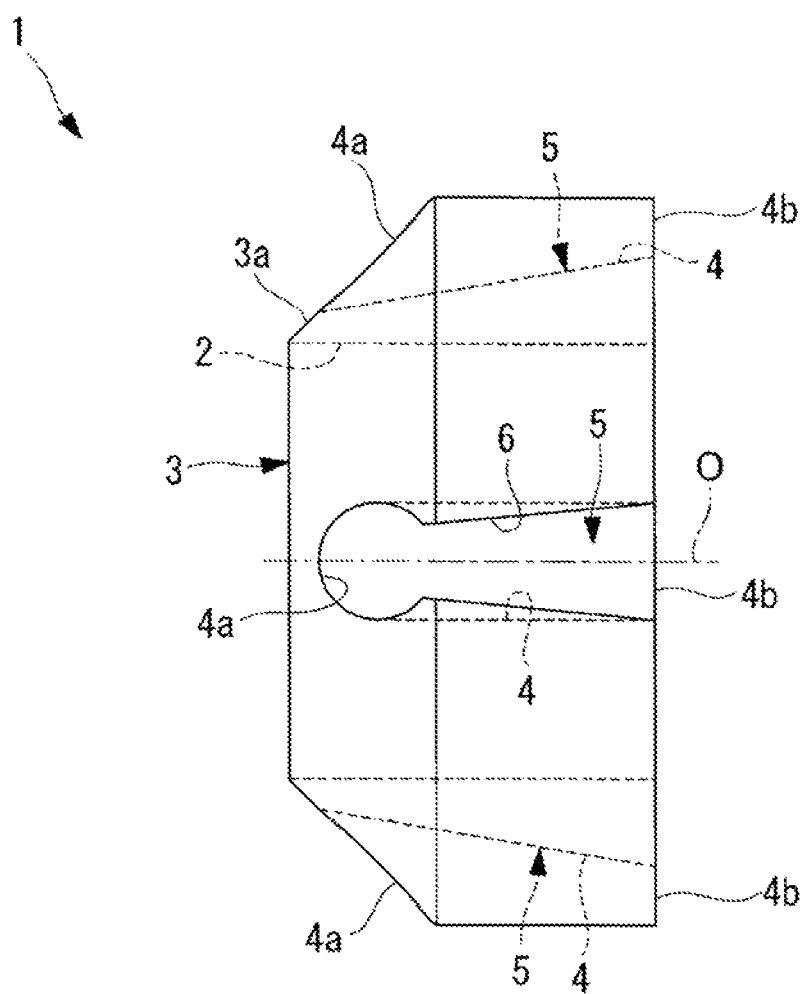
FIG. 2 is a side view depicting the medical instrument for endoscopic use in FIG. 1.
Figure 3:
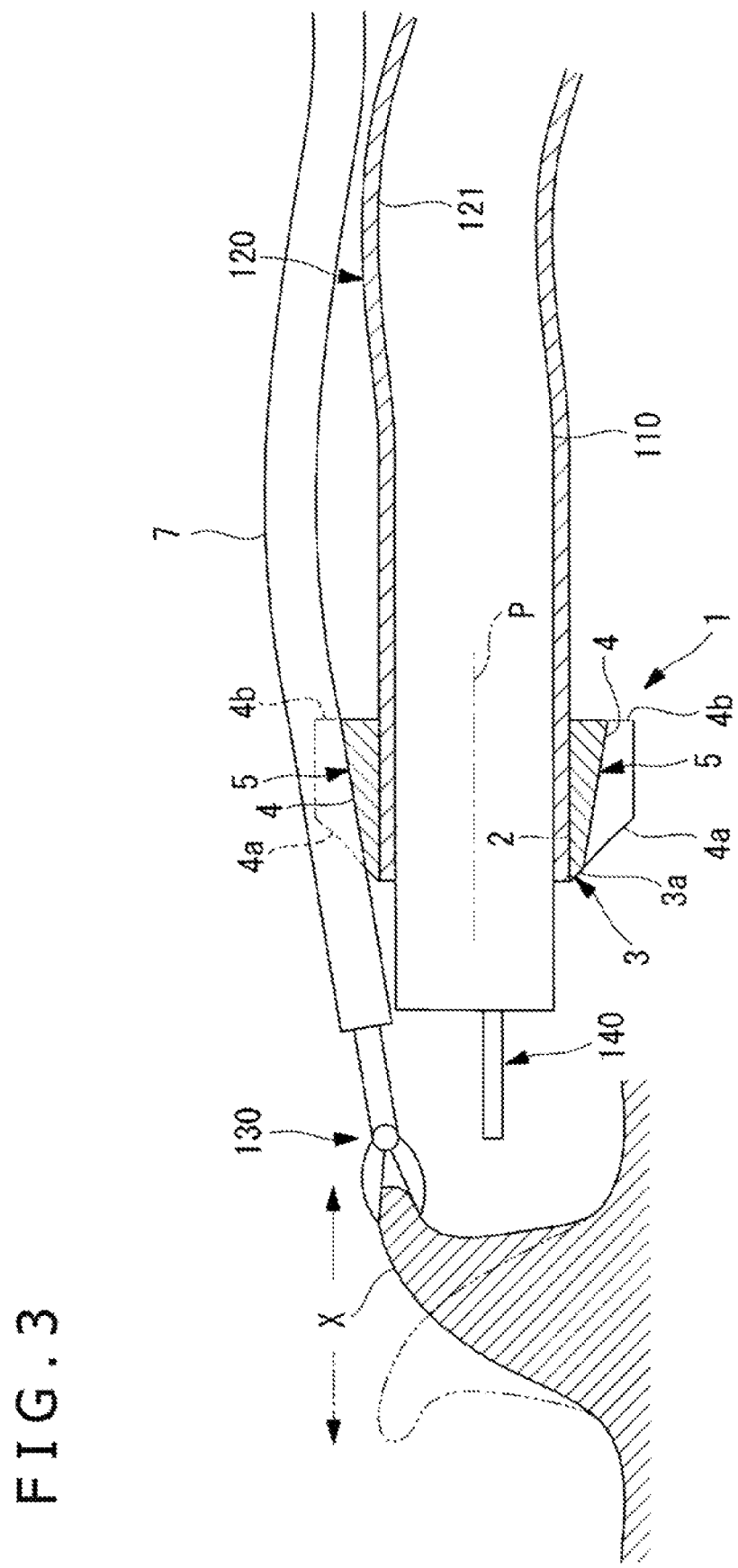
FIG. 3 is a longitudinal sectional view depicting a state in which the medical instrument for endoscopic use in FIG. 1 is fitted to a distal end portion of an over tube, a tube is attached to a channel, an endoscope is disposed in an inner hole of the over tube, and a tissue is held by a treatment tool projected from a distal end of the tube.

As depicted in FIGS. 1 to 3, the medical instrument for endoscopic use 1 according to the present embodiment is a ring-shaped attachment detachably attached to a distal end portion of a long over tube 120 having an inner hole 121 through which an endoscope 110 is made to penetrate. The medical instrument for endoscopic use 1 includes: a main body 3 having a central hole 2 of an inside diameter for fitting an outer peripheral surface of the distal end portion of the over tube 120; and channels 4 arranged in four positions of the main body 3 at equal intervals in a circumferential direction.

As depicted in FIG. 2, an outer peripheral surface of the main body 3 at one end in the direction of a central axis O is chamfered over an entire circumference. The channels 4 each extends along the direction of the central axis O of the main body 3. Each channel 4 includes a distal end opening 4a disposed in a chamfered surface 3a of the main body 3 and a proximal end opening 4b disposed in another end surface 3b in the direction of the central axis O. Each channel 4 is inclined in a direction of approaching the central axis O toward the distal end opening 4a from the proximal end opening 4b. Inclining means 5 is thereby formed.

Each channel 4 is opened outward in a radial direction by a slit 6. As depicted in FIG. 3, a long flexible tube 7 is fitted in the slit 6. The tube 7 can be attached to the channel 4 by inserting the tube 7 into the channel 4 from the slit 6 while compressing the tube 7 in the radial direction, and allowing the tube 7 to be restored by an elastic restoring force. The tube 7 may be bonded to the channel 4 by an adhesive. In addition, the tube 7 is preferably longer than the over tube 120.

Because the inclining means 5 is formed by inclining the channel 4 as described hereinbefore, the tube 7 fitted in the channel 4 is inclined in the direction of approaching the central axis O of the main body 3 toward a distal end.

The action of the thus formed medical instrument for endoscopic use 1 according to the present embodiment will be described in the following.

In order to treat an affected part X within the body of a patient by using the medical instrument for endoscopic use 1 according to the present embodiment, as depicted in FIG. 3, the distal end portion of the over tube 120 is fitted into the central hole 2 of the main body 3, and the distal end portion of the over tube 120 and the central hole 2 of the main body 3 are fixed to each other by a frictional force caused by the fitting or an adhesive. In addition, a distal end portion of a tube 7 is fitted to each channel 4 disposed in the main body 3, and the distal end portion of the tube 7 and the channel 4 are fixed to each other by a frictional force or an adhesive. The central axis O of the main body 3 and a longitudinal central axis P of the over tube 120 thereby coincide with each other.

Then, the endoscope 110 is inserted into the inner hole 121 of the over tube 120 from a proximal end side, and a front surface of the endoscope 110 is disposed in the vicinity of a distal end of the over tube 120.

In this state, the endoscope 110 is actuated. An assembly of the endoscope 110, the over tube 120, the medical instrument for endoscopic use 1 according to the present embodiment, and the tube 7 is inserted into a body while an image of the front of the over tube 120 is checked. The distal end of the over tube 120 is disposed at a position where the affected part X as a treatment target site is disposed within a field of view of the endoscope 110.

Then, one of the tubes 7 that is located on an upper side of the image obtained by the endoscope 110 is selected. A treatment tool 130 such as holding forceps is inserted from a proximal end of the tube 7. The treatment tool 130 is projected from the distal end of the tube 7 supported by the channel 4 of the main body 3.

With the medical instrument for endoscopic use 1 according to the present embodiment, the channel 4 attached to the distal end portion of the over tube 120 and supporting the tube 7 on an outside in a radial direction of the over tube 120 is inclined in a direction of approaching the longitudinal central axis P of the over tube 120 toward the front. Thus, by merely projecting the treatment tool 130 from the distal end of the tube 7, it is possible to make the treatment tool 130 appear within the image from the upper side of the image, move downward, and reach the affected part X disposed within the field of view.

As depicted in FIG. 3, a surrounding tissue of the affected part X is held by operating the treatment tool 130 that has reached the affected part X. The surrounding tissue held can be raised by merely moving the treatment tool 130 in a direction of pulling out the treatment tool 130 from the inside of the tube 7 to the proximal end side (solid line arrow in FIG. 3) or in a direction of pushing out the treatment tool 130 to a distal end side (alternate long and short dashed line arrow in FIG. 3).

Then, in this state, the raised tissue can be cut by displacing a treatment tool 140 such as an electric scalpel introduced via a channel not depicted but disposed in the endoscope 110, by advancing or retreating the endoscope 110 and operating a curving portion of the endoscope 110.

In this case, in the present embodiment, the treatment tool 130 raising the surrounding tissue is supported by the medical instrument for endoscopic use 1 attached to the over tube 120. Thus, the treatment tool 130 raising the surrounding tissue can be maintained in a stationary state irrespective of operation of the endoscope 110 at a time of cutting the tissue. In a case where the treatment tool 130 is attached to the endoscope 110 as in related art, the treatment tool 130 is moved in synchronism with the operation of the endoscope 110, and therefore the raised tissue is moved in synchronism with the operation of the endoscope 110. However, the medical instrument for endoscopic use 1 according to the present embodiment does not cause such an inconvenience, and can facilitate treatment.

In addition, in the present embodiment, the slits 6 open the channels 4 outward in the radial direction. Thus, a material thickness does not need to be secured on the outside in the radial direction. An outside diameter dimension of the main body 3 can therefore be reduced to improve ease of insertion of the main body 3 into the body.

Incidentally, while description has been made of a case where the tube 7 guiding the treatment tool 130 is attached to the channel 4 disposed in the main body 3 in the present embodiment, the treatment tool 130 may be used after being directly inserted into the channel 4.

In addition, while the channels 4 are arranged at four positions at equal intervals in the circumferential direction, the intervals do not have to be equal to each other, and the number of channels 4 may be any number as long as the number is one or more.

Figure 4:
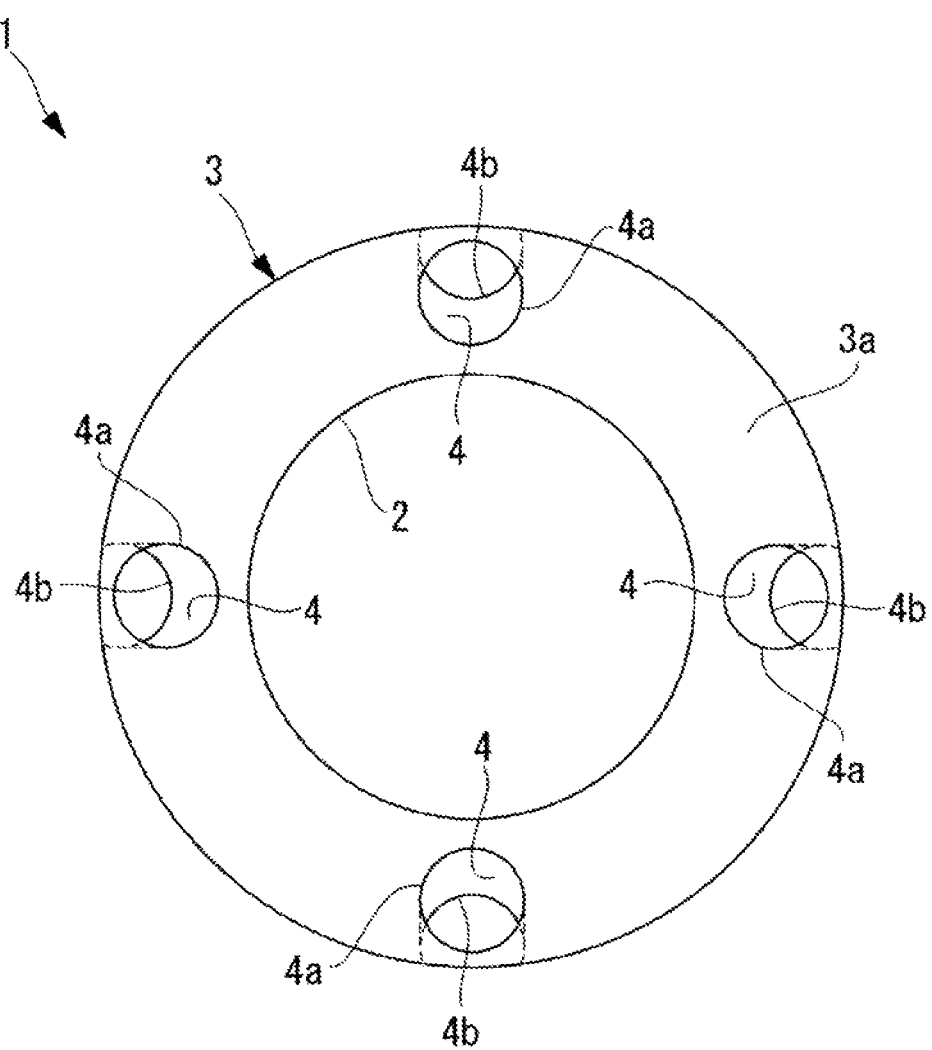
FIG. 4 is a front view depicting a modification of the medical instrument for endoscopic use in FIG. 1.
Figure 5:
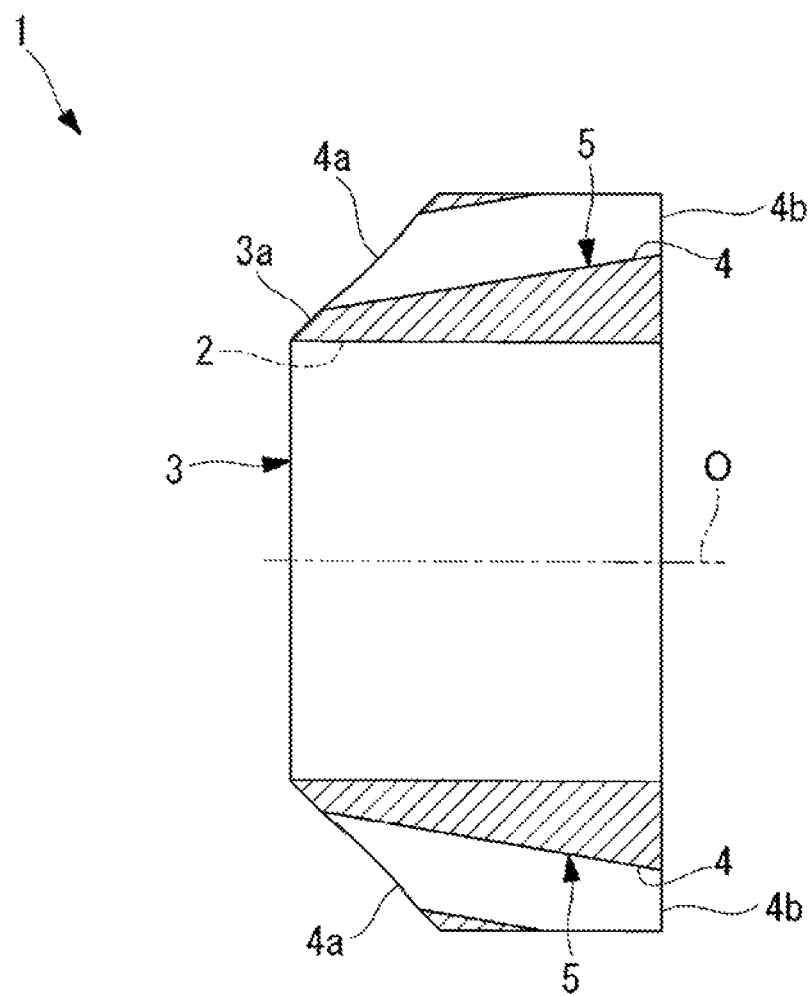
FIG. 5 is a longitudinal sectional view of the medical instrument for endoscopic use in FIG. 4.

In addition, as depicted in FIG. 4 and FIG. 5, the channels 4 may be closed on the outside in the radial direction. Thus, in a case where the treatment tool 130 is directly inserted into a channel 4, or in a case where a tube 7 is attached by fitting alone, the treatment tool 130 or the tube 7 can be prevented from coming off the channel 4 easily.

Figure 6:
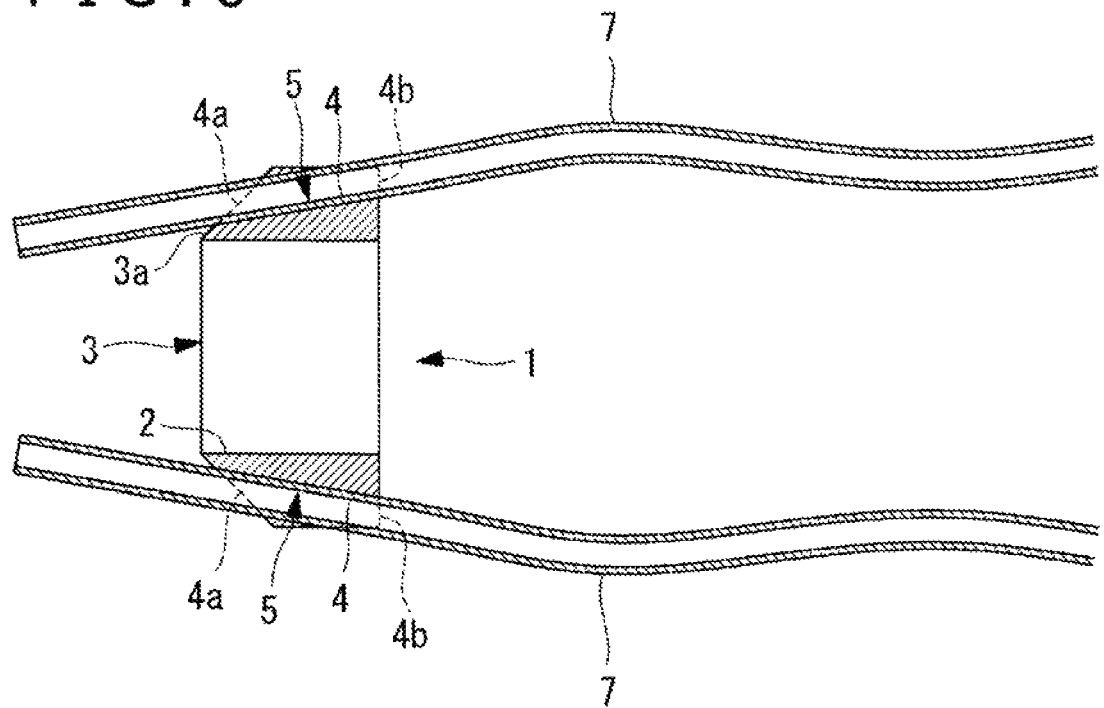
FIG. 6 is a longitudinal sectional view depicting another modification in which tubes are attached to respective channels of the medical instrument for endoscopic use in FIG. 4.
Figure 7:
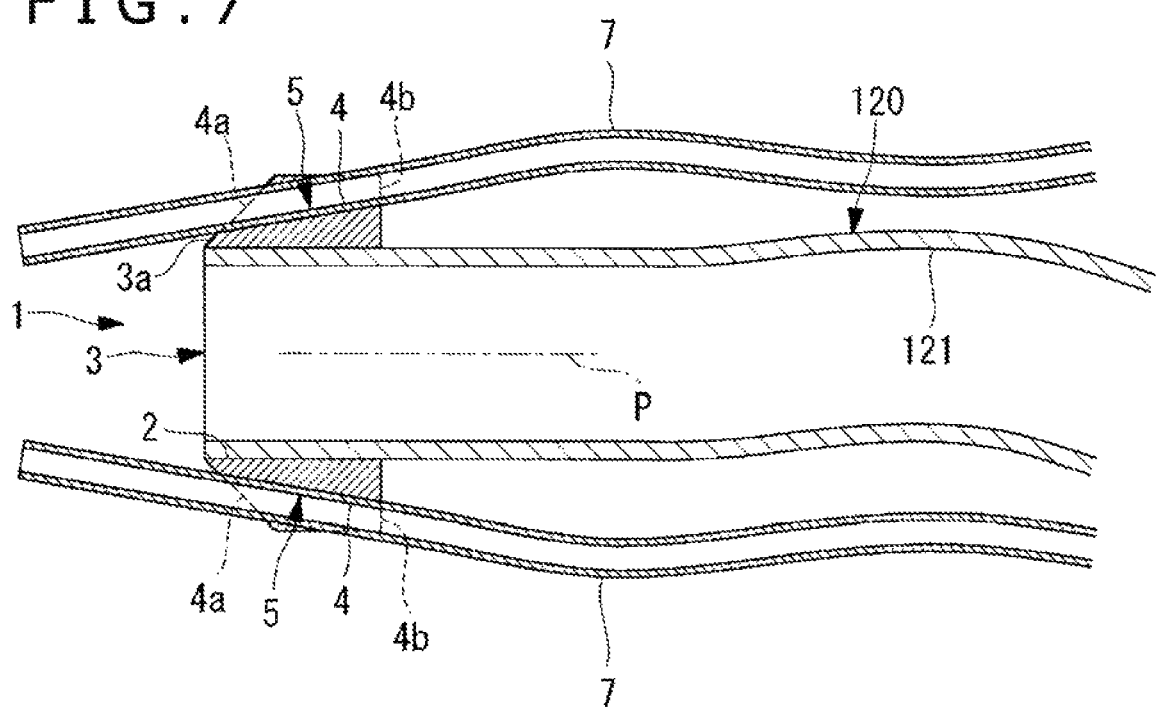
FIG. 7 is a longitudinal sectional view depicting another modification in which an over tube is attached to a central hole of the medical instrument for endoscopic use in FIG. 6.

In addition, only a ring-shaped attachment attached to the over tube 120 has been illustrated as the medical instrument for endoscopic use 1 according to the present embodiment. However, in place of this, a medical instrument obtained by attaching the tubes 7 to the channels 4 or integrally forming the tubes 7 and the channels 4 as depicted in FIG. 6 may be adopted, or a medical instrument obtained by fitting the over tube 120 or integrally forming the over tube 120 as depicted in FIG. 7 may be adopted.

Figure 8:
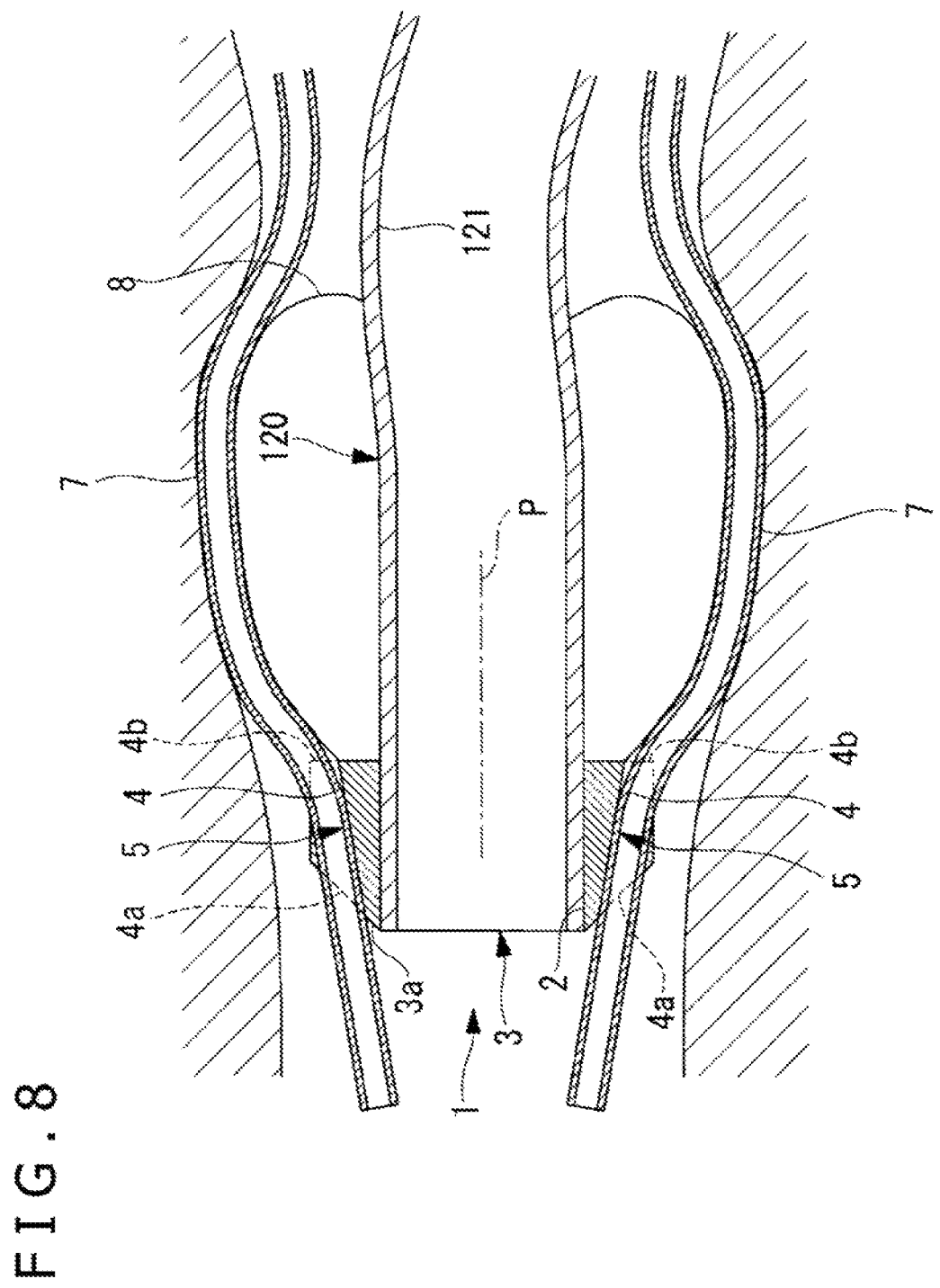
FIG. 8 is a longitudinal sectional view depicting another modification in which the over tube of the medical instrument for endoscopic use in FIG. 7 has a balloon.

In addition, as depicted in FIG. 8, the over tube 120 may include a balloon 8 capable of being expanded and contracted in the radial direction on the proximal end side as compared to the ring-shaped main body 3 and on an external surface of the over tube 120. When the balloon 8 is expanded in a case where an affected part X within a lumen is treated, the balloon 8 presses the tubes 7 outward in the radial direction of the over tube 120. The tubes 7 pressed outward in the radial direction and the expanded balloon 8 are pressed against the lumen to fix the over tube 120 to the lumen. The treatment can be thereby further facilitated.

Figure 11:
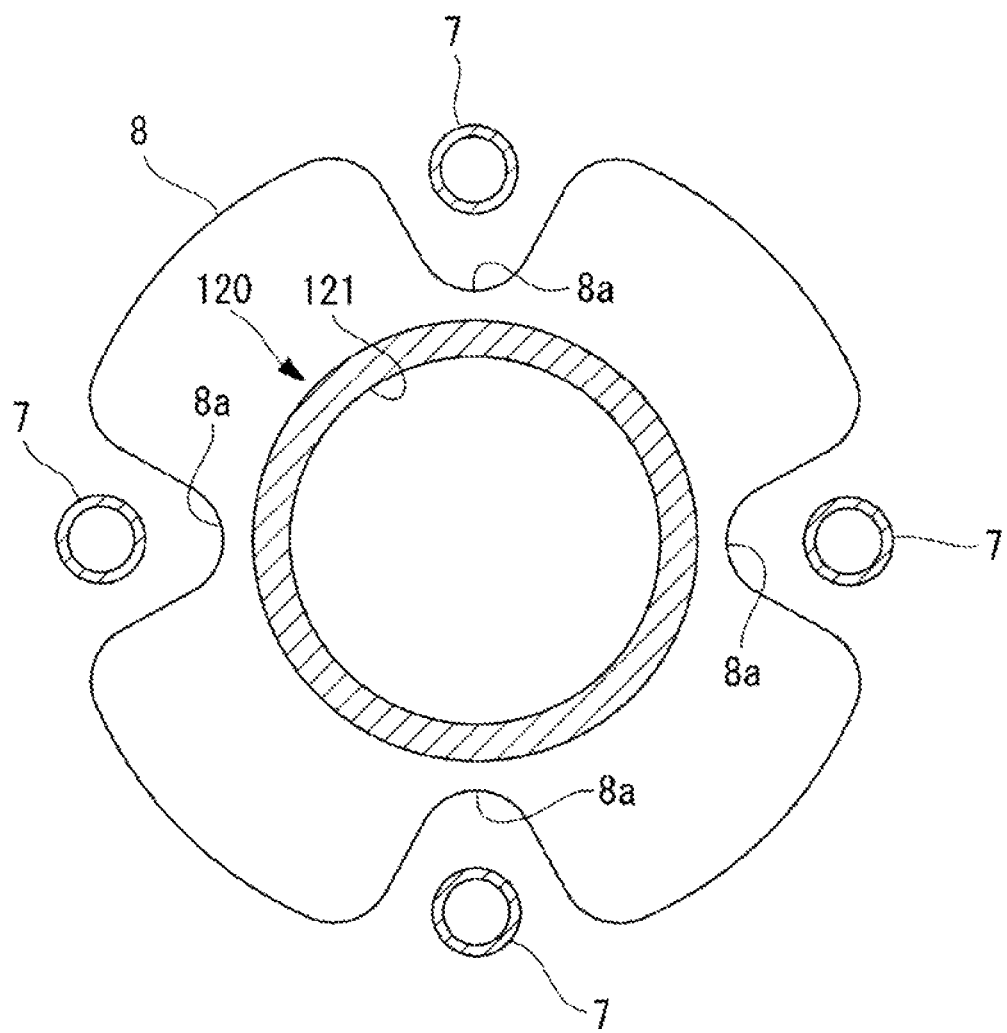
FIG. 11 is a longitudinal sectional view depicting another modification of the medical instrument for endoscopic use in FIG. 1.

In addition, as depicted in FIG. 11, the balloon 8 may include recessed portions 8a that become protrusive inward in the radial direction from a maximum outside diameter dimension of the balloon 8 when the balloon 8 is expanded. It is preferable that the recessed portions 8a have same phases as the tubes 7 and are arranged in the same number as that of tubes 7.

Consequently, when the balloon 8 is expanded, the balloon 8 is pressed against the lumen in a state in which the tubes 7 are arranged in the recessed portions 8a of the balloon 8. The over tube 120 can be thereby fixed to the lumen.

Figure 9:
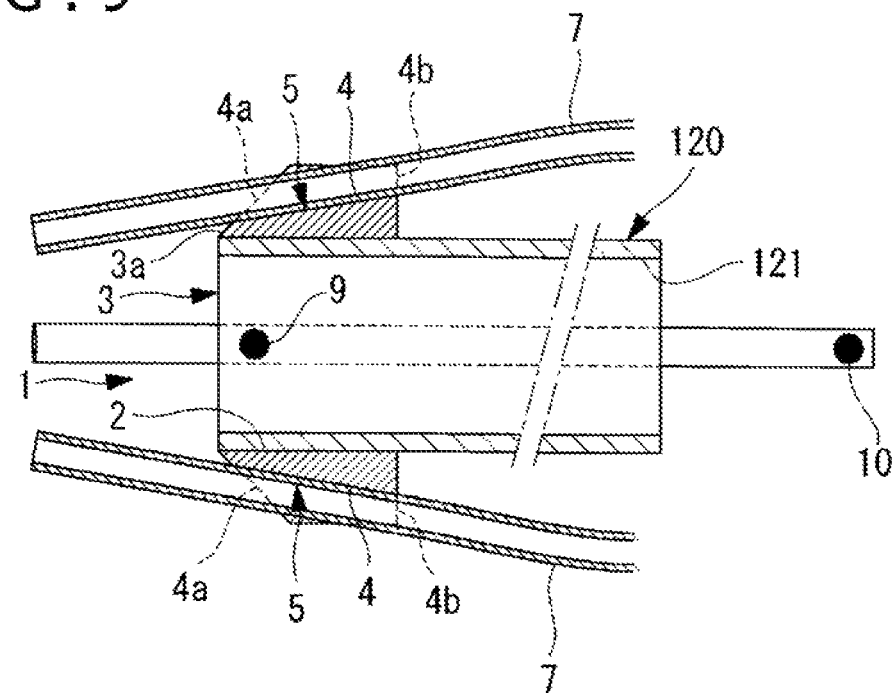
FIG. 9 is a diagram depicting an example of identifying indications for identifying a channel in the medical instrument for endoscopic use in FIG. 7.

In addition, in the present embodiment, four channels 4 are arranged at intervals in the circumferential direction, and the tubes 7 are attached to the respective channels 4. However, there is a case where the over tube 120 is twisted in a state of being inserted in a body, and it becomes unclear to which channel 4 a proximal end portion of a tube 7 exposed to the outside of the body corresponds. In order to resolve this inconvenience, as depicted in FIG. 9, marks 9 and 10, i.e. a distal end side identifying indication and a proximal end side identifying indication, which associate the inner surface of the distal end of the over tube 120 and the proximal end of the tube 7 with each other, may be respectively arranged on the inner surface of the distal end of the over tube 120 and the proximal end of the tube 7.

Thus, the mark 9 on the inner surface of the over tube 120 can be disposed within the field of view of the endoscope 110 by disposing the endoscope 110 in a position retracted to the proximal end side with respect to the over tube 120. A mark 10 of a different shape or color is provided for each channel 4 to which a tube 7 is attached. The position of the channel 4 to which the tube 7 is attached can thereby be recognized, i.e. identified, based on the mark 10 on the proximal end side of the tube 7.

In other words, the treatment tool 130 can be projected on the upper side in the endoscope image by selecting the tube 7 disposed on the upper side in the endoscope image and corresponding to the mark 10, and inserting the treatment tool 130 from the proximal end side of the tube 7.

It is to be noted that the mark 9 is not limited to being disposed on the inner surface of the inner hole 121 of the over tube 120. The over tube 120 may be formed of a transparent material, and the mark 9 may be disposed in some position visually recognizable from the inside of the inner hole 121 of the over tube 120 by the endoscope 110, the position being a position on the outer surface of the over tube 120, the inner surface of the central hole 2 of the medical instrument for endoscopic use 1 into which hole the outer surface of the over tube 120 is fitted, or the like.

Figure 10:
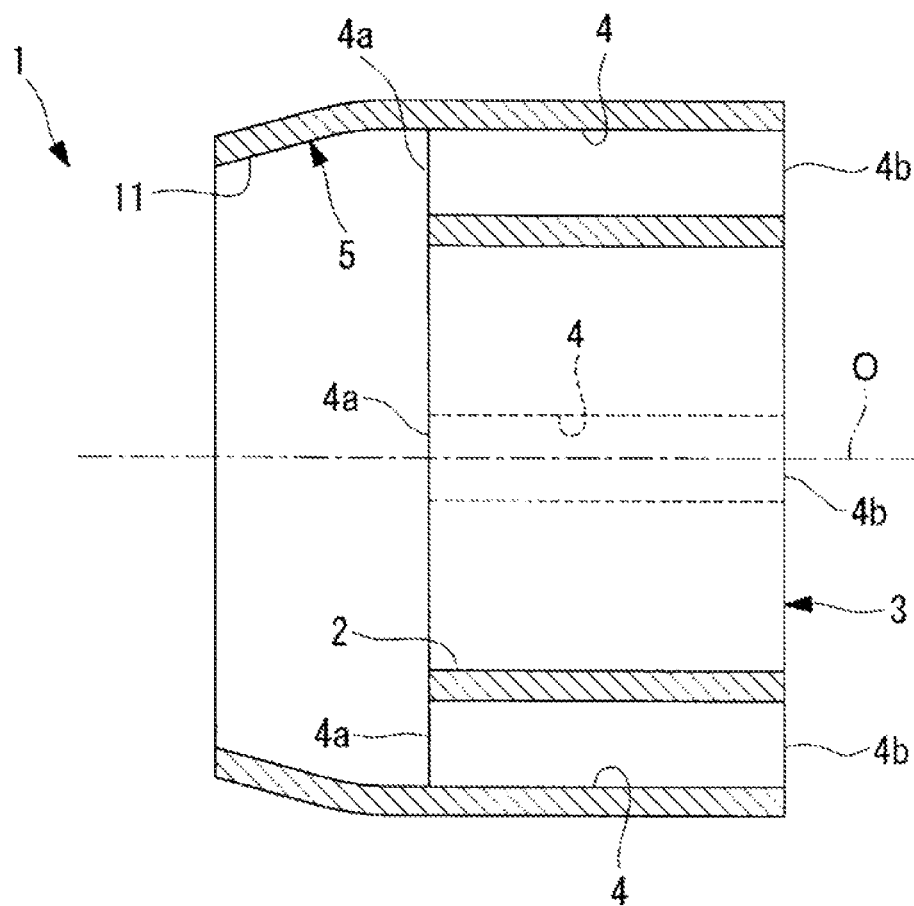
FIG. 10 is a longitudinal sectional view depicting another modification of the medical instrument for endoscopic use in FIG. 1.

In addition, in the present embodiment, a case has been illustrated in which a channel 4 itself is inclined as the inclining means 5 for inclining and projecting the treatment tool 130 inserted in the channel 4 in a direction toward the central axis O. However, the inclining means 5 is not limited to this. For example, as depicted in FIG. 10, the channel 4 itself may be arranged substantially in parallel with the central axis O, and an inclining surface 11, i.e. a guide surface, which guides the treatment tool 130 projected from the distal end opening 4a of the channel 4 toward the inside in the radial direction, may be disposed in front of the channel 4. The inclining surface 11 may be disposed over the whole circumference in the circumferential direction as depicted in FIG. 10, or may be disposed partially in circumferential positions corresponding to the channels 4. In this case, the outer peripheral surface at one end of the main the body portion 3 may not be chamfered.

In sum, one aspect of the disclosed technology is directed to a medical instrument for endoscopic use. The medical instrument comprises an elongated open ended over tube configured to receive an endoscope in a direction along a longitudinal central axis of the over tube. The endoscope travels retractably from a distal end of the over tube. A tube is disposed concentrically outwardly of the over tube so that a treatment tool is inserted through the tube and is projected forwardly with respect to the over tube from a distal end of the tube. A balloon is disposed on an external surface of the over tube and is expandable outwardly in a radial direction of the over tube.

The balloon expands outwardly in the radial direction of the over tube while maintaining a state of being separated from the tube. The balloon include at least one of recessed portion that become protrusive inward in the radial direction from a maximum outside diameter dimension of the balloon when the balloon is expanded and the tube is placed in the recess portion. The balloon is disposed between the over tube and the tube and presses the tube outwardly by expanding in the radial direction. A plurality of tubes are disposed at intervals in a circumferential direction of the over tube. The medical instrument further comprises a main body disposed on a distal end portion of the over tube and having a channel retaining the tube therein. The main body has inclining means for inclining the tube toward a front in a direction of approaching a longitudinal central axis of the over tube. At least one of the plurality of tubes has a proximal end side mark so as to be distinguishable by an operator. A distal end side mark corresponding to the proximal end side mark and is disposed in a position visually recognizable from an inner surface side of the over tube. The medical instrument for endoscopic use further comprises a flexible endoscope that is inserted into the over tube.

Another aspect of the disclosed technology is directed to a medical instrument for endoscopic use. The medical instrument comprises an elongated open ended over tube configured to receive an endoscope in a direction along a longitudinal central axis of the over tube. The endoscope travels retractably from a distal end of the over tube. A first tube is disposed concentrically outwardly of the over tube so that the treatment tool is inserted through the first tube projected forwardly with respect to the over tube from a distal end of the first tube. A second tube is disposed concentrically outwardly of the over tube so that a treatment tool is inserted through the second tube and is projected forwardly with respect to the over tube from a distal end of the second tube so as to be separated from the first tube. A balloon is disposed on an external surface of the over tube and is expandable between the first tube and the second tube and outwardly in a radial direction of the over tube and the balloon at a time of expansion being located radially outwardly of the first tube and the second tube.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A medical instrument for endoscopic use, the medical instrument comprising:
    an elongated open ended over tube configured to receive an endoscope in a direction along a longitudinal central axis of the over tube;
    a tube disposed concentrically outwardly of the over tube, the tube being configured to receive a treatment tool such that the treatment tool can extend from a distal end of the tube so as to be projected distally with respect to a distal end of the over tube; and
    a balloon disposed on an external surface of the over tube and being expandable outwardly in a radial direction of the over tube,
    wherein the balloon includes at least one recessed portion that is recessed inwardly in the radial direction from a maximum outside diameter dimension of the balloon when the balloon is expanded, and the tube is arranged in the at least one recessed portion.

2. The medical instrument of claim 1, wherein the balloon is disposed between the over tube and the tube and is configured to press the tube outwardly by expanding in the radial direction.

3. The medical instrument of claim 1, wherein a plurality of tubes are disposed at intervals in a circumferential direction of the over tube.

4. The medical instrument of claim 3, wherein at least one of the plurality of tubes includes a proximal end side mark so as to be distinguishable by an operator.

5. The medical instrument of claim 4, wherein a distal end side mark corresponding to the proximal end side mark is disposed in a position visually recognizable from an inner surface side of the over tube.

6. The medical instrument of claim 1, further comprising a flexible endoscope inserted into the over tube.

7. A medical instrument for endoscopic use, the medical instrument comprising:
    an elongated open ended over tube configured to receive an endoscope in a direction along a longitudinal central axis of the over tube;
    a tube disposed concentrically outwardly of the over tube, the tube being configured to receive a treatment tool such that the treatment tool can extend from a distal end of the tube so as to be projected distally with respect to a distal end of the over tube;
    a balloon disposed on an external surface of the over tube and being expandable outwardly in a radial direction of the over tube; and
    a main body disposed on a distal end portion of the over tube and including a channel retaining the tube therein, wherein the channel is inclined with respect to the longitudinal central axis of the over tube such that the tube extends through the channel in a distal direction so as to be inclined in a direction toward the longitudinal central axis of the over tube.

8. The medical instrument of claim 7, wherein the balloon includes at least one recessed portion that is recessed inwardly in the radial direction from a maximum outside diameter dimension of the balloon when the balloon is expanded, and the tube is arranged in the at least one recessed portion.

9. A medical instrument for endoscopic use, the medical instrument comprising:
- an elongated open ended over tube configured to receive an endoscope in a direction along a longitudinal central axis of the over tube;
- a first tube disposed concentrically outwardly of the over tube, the first tube being configured to receive a first treatment tool such that the first treatment tool can extend from a distal end of the first tube so as to be projected distally with respect to the over tube;
- a second tube disposed concentrically outwardly of the over tube, the second tube being configured to receive a second treatment tool such that the second treatment tool can extend from a distal end of the second tube so as to be projected distally with respect to the over tube and so as to be separated from the first tube; and
- a balloon that is disposed on an external surface of the over tube and is expandable between the first tube and the second tube and outwardly in a radial direction of the over tube, wherein the balloon at a time of expansion is located radially outwardly of the first tube and the second tube.

* * * * *